(12) United States Patent
Cornelisse et al.

(10) Patent No.: US 11,057,724 B2
(45) Date of Patent: Jul. 6, 2021

(54) SYSTEMS AND METHODS FOR FITTING A HEARING DEVICE

(71) Applicant: SONOVA AG, Staefa (CH)

(72) Inventors: Leonard E. Cornelisse, Waterloo (CA); Galen Dunning, Kitchener (CA); Isaac W. Hamp, Kitchener (CA); Edward Chau, Waterloo (CA)

(73) Assignee: Sonova AG, Staefa (CH)

( * ) Notice: Subject to any disclaimer, the term of this patent is extended or adjusted under 35 U.S.C. 154(b) by 157 days.

(21) Appl. No.: 16/580,837

(22) Filed: Sep. 24, 2019

(65) Prior Publication Data

US 2021/0092538 A1 Mar. 25, 2021

(51) Int. Cl.
*H04R 25/00* (2006.01)
*A61B 5/12* (2006.01)

(52) U.S. Cl.
CPC ............. *H04R 25/70* (2013.01); *A61B 5/123* (2013.01); *H04R 25/505* (2013.01); *H04R 2225/43* (2013.01)

(58) Field of Classification Search
CPC combination set(s) only.
See application file for complete search history.

(56) References Cited

U.S. PATENT DOCUMENTS

| 9,414,173 | B1* | 8/2016 | Hou | H04R 25/70 |
| 2004/0264719 | A1* | 12/2004 | Naylor | G16H 20/30 |
| | | | | 381/314 |
| 2009/0046878 | A1* | 2/2009 | Sorgel | H04R 25/305 |
| | | | | 381/314 |
| 2010/0316227 | A1 | 12/2010 | Schmid | |
| 2017/0366904 | A1* | 12/2017 | Oetting | H03G 9/025 |
| 2018/0166092 | A1* | 6/2018 | Tu | H04R 25/356 |

FOREIGN PATENT DOCUMENTS

WO 2008141672 11/2008

* cited by examiner

*Primary Examiner* — Ryan Robinson
*Assistant Examiner* — Angelica M McKinney
(74) *Attorney, Agent, or Firm* — ALG Intellectual Property, LLC

(57) ABSTRACT

An exemplary hearing device is configured to be fit for a user. The hearing device maintains data representative of a first and a second fitting strategy for the hearing device, the first and the second fitting strategy comprising a first and a second set of values, respectively, for a plurality of parameters that specify an operation of the hearing device. The hearing device receives a value for a mixing setting that specifies a weighting between the first and the second fitting strategy. The hearing device determines, based on the value for the mixing setting, a custom fitting strategy comprising a custom set of values for the plurality of parameters, the custom set of values including combinations of the first and second sets of values that are weighted in accordance with the value for the mixing setting. The hearing device bases outputting of a signal on the custom fitting strategy.

20 Claims, 15 Drawing Sheets

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| | 172 | 345 | 517 | 689 | 861 | 1034 | 1206 | 1378 | 1550 | 1723 | 1981 | 2326 | 2670 | 3015 | 3445 | 4048 | 4823 | 5943 | 7494 | 9647 |
| MaxXspace_X | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| MinXspace_X | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| SLim | 95.3 | 94.6 | 95.3 | 94.9 | 95.5 | 95.1 | 95.5 | 95.5 | 96.1 | 95.7 | 96.4 | 97.1 | 98.6 | 101.9 | 101.9 | 95.2 | 92.4 | 87.6 | 85.7 | 83.2 |
| GcLoud | 12.1 | 7.2 | 5.4 | 3.4 | 3.6 | 3.2 | 3.6 | 3.6 | 4.2 | 3.8 | 4.5 | 5.2 | 6.7 | 10.0 | 10.0 | 2.0 | -5.5 | -10.3 | -12.2 | -14.7 |
| GcMid | 12.1 | 7.2 | 5.4 | 3.4 | 3.6 | 3.2 | 3.6 | 3.6 | 4.2 | 3.8 | 4.5 | 5.2 | 6.7 | 10.0 | 10.0 | 2.0 | -5.5 | -10.3 | -12.2 | -14.7 |
| GcSoft | 38.0 | 36.0 | 35.0 | 40.0 | 39.0 | 38.0 | 38.0 | 38.0 | 39.0 | 39.0 | 37.0 | 37.0 | 36.0 | 39.0 | 39.0 | 36.0 | 38.0 | 33.0 | 31.0 | 25.0 |
| GcQuiet | 38.0 | 36.0 | 35.0 | 40.0 | 39.0 | 38.0 | 38.0 | 38.0 | 39.0 | 39.0 | 37.0 | 37.0 | 36.0 | 39.0 | 39.0 | 36.0 | 38.0 | 33.0 | 31.0 | 25.0 |
| EkLoud | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |
| EkMid | 86.3 | 85.2 | 86.1 | 84.1 | 82.2 | 80.8 | 79.1 | 77.8 | 76.9 | 76.1 | 76.3 | 72.8 | 72.6 | 72.3 | 72.1 | 72.7 | 72.6 | 72.3 | 71.3 | 67.1 |
| EkSoft | 44.3 | 43.2 | 44.1 | 42.1 | 40.2 | 38.0 | 37.1 | 35.8 | 34.9 | 34.1 | 34.3 | 30.8 | 30.6 | 30.3 | 30.1 | 30.7 | 30.6 | 30.3 | 29.3 | 25.1 |
| EkQuiet | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| SLim | 78.7 | 78.0 | 78.7 | 78.3 | 78.9 | 78.5 | 78.9 | 78.9 | 79.5 | 79.1 | 79.8 | 80.5 | 82.0 | 85.3 | 85.3 | 78.6 | 75.8 | 71.0 | 69.1 | 66.6 |
| GcLoud | 3.8 | -1.1 | -2.9 | -5.0 | -4.7 | -5.1 | -4.7 | -4.7 | -4.1 | -4.5 | -3.8 | -3.1 | -1.6 | 1.7 | 1.7 | -6.3 | -13.8 | -18.6 | -20.5 | -23.0 |
| GcMid | 3.8 | -1.1 | -2.9 | -5.0 | -4.7 | -5.1 | -4.7 | -4.7 | -4.1 | -4.5 | -3.8 | -3.1 | -1.6 | 1.7 | 1.7 | -6.3 | -13.8 | -18.6 | -20.5 | -23.0 |
| GcSoft | 8.9 | 2.9 | -0.7 | -2.4 | -3.0 | -3.1 | -3.1 | -3.1 | -3.0 | -3.0 | -3.2 | -3.2 | -3.3 | -3.0 | -3.0 | -3.3 | -3.1 | -3.6 | -3.8 | -4.4 |
| GcQuiet | 8.9 | 2.9 | -0.7 | -2.4 | -3.0 | -3.1 | -3.1 | -3.1 | -3.0 | -3.0 | -3.2 | -3.2 | -3.3 | -3.0 | -3.0 | -3.3 | -3.1 | -3.6 | -3.8 | -4.4 |
| EkLoud | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |
| EkMid | 78.0 | 76.9 | 77.8 | 75.8 | 73.9 | 72.5 | 70.8 | 69.5 | 68.6 | 67.8 | 68.0 | 64.5 | 64.3 | 64.0 | 63.8 | 64.4 | 64.3 | 64.0 | 63.0 | 58.8 |
| EkSoft | 27.7 | 26.6 | 27.5 | 25.5 | 23.6 | 22.2 | 20.5 | 19.2 | 18.3 | 17.5 | 17.7 | 14.2 | 14.0 | 13.7 | 13.5 | 14.1 | 14.0 | 13.7 | 12.7 | 8.5 |
| EkQuiet | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |

Fig. 5

| Hz | 172 | 345 | 517 | 689 | 861 | 1034 | 1206 | 1387 | 1550 | 1723 | 1981 | 2326 | 2670 | 3015 | 3445 | 4048 | 4823 | 5943 | 7494 | 9647 |
|---|---|---|---|---|---|---|---|---|---|---|---|---|---|---|---|---|---|---|---|---|
| Effective X | 0.39 | 0.41 | 0.41 | 0.41 | 0.45 | 0.45 | 0.45 | 0.45 | 0.45 | 0.45 | 0.45 | 0.5 | 0.52 | 0.52 | 0.52 | 0.52 | 0.52 | 0.52 | 0.52 | 0.52 |

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| MaxX | 172 | 345 | 517 | 689 | 861 | 1034 | 1206 | 1378 | 1550 | 1723 | 1981 | 2326 | 2670 | 3015 | 3445 | 4048 | 4823 | 5943 | 7494 | 9647 |
| | 1 | 1 | 1 | 1 | 1 | 1 | 1 | 1 | 1 | 1 | 1 | 1 | 1 | 1 | 1 | 1 | 1 | 1 | 1 | 1 |
| MinX | 0 | 0 | 0 | 0 | 0 | 0 | 0 | 0 | 0 | 0 | 0 | 0 | 0 | 0 | 0 | 0 | 0 | 0 | 0 | 0 |
| DMPO | 6 | 6 | 6 | 6 | 6 | 6 | 6 | 6 | 6 | 6 | 6 | 8 | 8 | 10 | 10 | 8 | 8 | 6 | 4 | 4 |
| DGcLoud | 6 | 10 | 6 | 6 | 6 | 6 | 6 | 6 | 6 | 6 | 6 | 8 | 8 | 10 | 10 | 8 | 8 | 6 | 4 | 4 |
| DGcMid | 8 | 8 | 8 | 8 | 8 | 8 | 8 | 8 | 8 | 8 | 8 | 10 | 10 | 12 | 12 | 10 | 10 | 8 | 6 | 6 |
| DGcSoft | 10 | 10 | 10 | 10 | 10 | 10 | 10 | 10 | 10 | 10 | 10 | 12 | 12 | 14 | 14 | 12 | 12 | 10 | 8 | 8 |
| DGcQuiet | 12 | 12 | 12 | 12 | 12 | 12 | 12 | 12 | 12 | 12 | 12 | 14 | 14 | 16 | 16 | 14 | 14 | 12 | 10 | 10 |
| DEkLoud | 6 | 6 | 6 | 6 | 6 | 6 | 6 | 6 | 6 | 6 | 6 | 8 | 10 | 10 | 8 | 8 | 6 | 6 | 4 | 4 |
| DEkMid | 6 | 6 | 6 | 6 | 6 | 6 | 6 | 6 | 6 | 6 | 6 | 8 | 10 | 10 | 8 | 8 | 6 | 6 | 4 | 4 |
| DEkSoft | 6 | 6 | 6 | 6 | 6 | 6 | 6 | 6 | 6 | 6 | 6 | 8 | 10 | 10 | 8 | 8 | 6 | 6 | 4 | 4 |
| DEkQuiet | 6 | 6 | 6 | 6 | 6 | 6 | 6 | 6 | 6 | 6 | 6 | 8 | 10 | 10 | 8 | 8 | 6 | 6 | 4 | 4 |
| DMPO | -12 | -12 | -12 | -12 | -12 | -12 | -12 | -12 | -12 | -12 | -12 | -10 | -10 | -8 | -8 | -10 | -10 | -12 | -14 | -14 |
| DGcLoud | -12 | -10 | -12 | -12 | -12 | -12 | -12 | -12 | -12 | -12 | -12 | -10 | -10 | -8 | -8 | -10 | -10 | -12 | -14 | -14 |
| DGcMid | -10 | -10 | -10 | -10 | -10 | -10 | -10 | -10 | -10 | -10 | -10 | -8 | -8 | -6 | -6 | -8 | -8 | -10 | -12 | -12 |
| DGcSoft | -8 | -8 | -8 | -8 | -8 | -8 | -8 | -8 | -8 | -8 | -8 | -6 | -6 | -4 | -4 | -6 | -6 | -8 | -10 | -10 |
| DGcQuiet | -6 | -6 | -6 | -6 | -6 | -6 | -6 | -6 | -6 | -6 | -6 | -4 | -4 | -4 | -4 | -4 | -4 | -6 | -8 | -8 |
| DEkLoud | -12 | -12 | -12 | -12 | -12 | -12 | -12 | -12 | -12 | -12 | -12 | -10 | -10 | -8 | -8 | -10 | -10 | -12 | -14 | -14 |
| DEkMid | -12 | -12 | -12 | -12 | -12 | -12 | -12 | -12 | -12 | -12 | -12 | -10 | -10 | -8 | -8 | -10 | -10 | -12 | -14 | -14 |
| DEkSoft | -12 | -12 | -12 | -12 | -12 | -12 | -12 | -12 | -12 | -12 | -12 | -10 | -10 | -8 | -8 | -10 | -10 | -12 | -14 | -14 |
| DEkQuiet | -12 | -12 | -12 | -12 | -12 | -12 | -12 | -12 | -12 | -12 | -12 | -10 | -10 | -8 | -8 | -10 | -10 | -12 | -14 | -14 |

SYSTEMS AND METHODS FOR FITTING A HEARING DEVICE

BACKGROUND INFORMATION

Hearing devices may be configured with a wide range of settings to provide sound that may be personally fit for individual users. Conventional hearing devices are often fit by a hearing health care professional using sophisticated models and complex software to set a large number of parameters on the hearing device. Alternatively, conventional hearing devices provide a limited number of predefined settings from which the user may select to define the fitting on the hearing device. However, these two approaches for fitting conventional hearing devices provide limited options for the user. The user may have to either choose between limited predefined settings for self-fitting the hearing device, or otherwise depend on the hearing health care professional to make any adjustments to the fitting.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 2-8 illustrate exemplary implementations of a fitting strategy for a hearing device according to principles described herein.

DETAILED DESCRIPTION

Exemplary systems and methods for fitting a hearing device are described herein. For example, a hearing device may comprise a memory storing instructions and a processor communicatively coupled to the memory. The processor may be configured to execute the instructions to maintain data representative of a first fitting strategy for the hearing device. The first fitting strategy may comprise a first set of values for a plurality of parameters that specify an operation of the hearing device. The processor may be further configured to execute the instructions to maintain data representative of a second fitting strategy for the hearing device, the second fitting strategy comprising a second set of values for the plurality of parameters. The processor may receive a value for a mixing setting that specifies a weighting between the first fitting strategy and the second fitting strategy. Based on the value for the mixing setting, the processor may determine a custom fitting strategy comprising a custom set of values for the plurality of parameters, the custom set of values including combinations of the first and second sets of values that are weighted in accordance with the weighting specified by the value for the mixing setting. The processor may be further configured to direct the hearing device to output a signal based on the custom fitting strategy.

The systems and methods described herein may advantageously provide many benefits to users of hearing devices. For example, the hearing devices described herein may provide more ways to personalize and/or customize a fit of the hearing devices than conventional hearing devices. Further, the fitting strategies for the hearing devices may allow the hearing devices to more accurately compensate for progressions in hearing loss and for the user to more easily adjust the hearing devices than conventional hearing devices. Additionally, the fitting strategies described herein may allow for interoperability between fitting of the hearing device performed by a hearing health care professional and the user.

For at least these reasons, the systems and methods described herein may advantageously increase performance, reliability, and ease of use for hearing device users compared to conventional hearing devices. These and other benefits of the systems and methods described herein will be made apparent herein.

Figure 1:
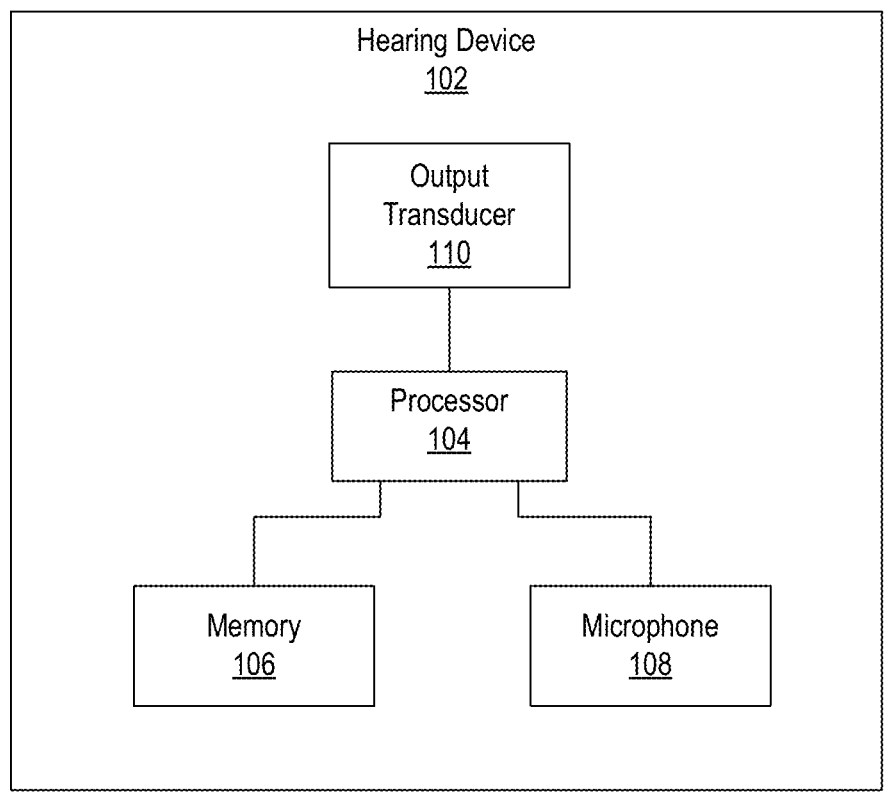
FIG. 1 shows an exemplary configuration of a hearing device according to principles described herein.

FIG. 1 shows an exemplary configuration of a hearing device 102. Hearing device 102 may be implemented by any type of device configured to provide or enhance hearing to a user. For example, hearing device 102 may be implemented by a hearing aid configured to provide an audible signal (e.g., amplified audio content) to a user, a sound processor included in a system configured to apply both acoustic and electrical stimulation representative of audio content to a user, a receiver-in-canal (RIC) hearing device, or any other suitable hearing prosthesis. As shown, hearing device 102 includes a processor 104 communicatively coupled to a memory 106, a microphone 108, and an output transducer 110. Hearing device 102 may include additional or alternative components as may serve a particular implementation.

Microphone 108 may be implemented by any suitable audio detection device and is configured to detect audio content ambient to a user of hearing device 102. Microphone 108 may be included in or communicatively coupled to hearing device 102 in any suitable manner.

Output transducer 110 may be implemented by any suitable audio output device, such as a loudspeaker of a hearing device or an output electrode of a cochlear implant system.

Memory 106 may be implemented by any suitable type of storage medium and may be configured to maintain (e.g., store) data generated, accessed, or otherwise used by processor 104. For example, memory 106 may maintain fitting strategy data, hearing loss compensation data, audio processing data, etc.

Processor 104 may be configured to perform various processing operations, such as configuring fitting strategies for the hearing device, and receiving and processing audio content output by a receiver. Processor 104 may be implemented by any suitable combination of hardware and software. In the description that follows, any references to operations performed by hearing device 102 may be understood to be performed by processor 104 of hearing device 102.

Figure 2:
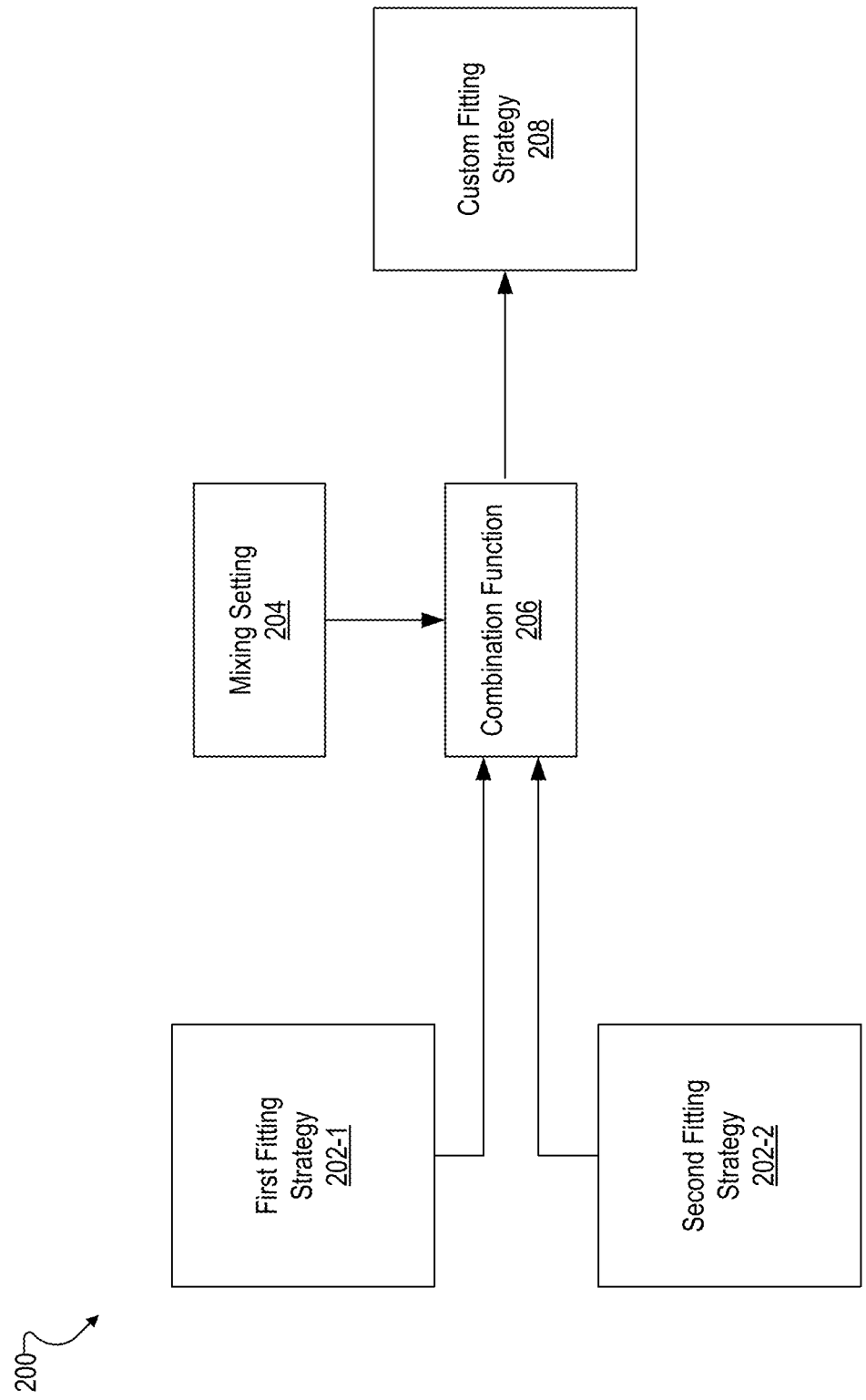

FIG. 2 illustrates an exemplary implementation 200 of a fitting strategy for a hearing device (e.g., hearing device 102). Implementation 200 may be implemented, for example, by processor 104 of hearing device 102. Implementation 200 includes a first fitting strategy 202-1 and a second fitting strategy 202-2 (collectively, fitting strategies 202). Fitting strategies 202 may each include one or more sets of values for a plurality of parameters that specify an operation of hearing device 102. The parameters may include any suitable parameters, such as amplification parameters, noise reduction parameters, speech enhancement parameters, etc., which may include such parameters as gain levels, knee points, compression ratios, maximum outputs, feedback cancelation strength, directionality strength, strength characteristics, frequency characteristics, etc.

Hearing device 102 may receive a value for a mixing setting 204 that specifies a weighting between first fitting strategy 202-1 and second fitting strategy 202-2. Implementation 200 also includes a combination function 206 that receives inputs including mixing setting 204, first fitting strategy 202-1, and second fitting strategy 202-2 and determines a custom fitting strategy 208 based on the received inputs.

For example, first fitting strategy 202-1 may include a set of maximum values implemented by hearing device 102 for the plurality of parameters. Thus, applying first fitting strategy 202-1 on hearing device 102 may provide a highest amount of amplification for which hearing device 102 is configured. Conversely, second fitting strategy 202-2 may include a set of minimum values implemented by hearing device 102 for the plurality of parameters. Thus, applying second fitting strategy 202-2 on hearing device 102 may provide a lowest amount of amplification for which hearing device 102 is configured. In this example, mixing setting 204 may be implemented as a single value between 0 and 1 that specifies a weighting between first fitting strategy 202-1 and second fitting strategy 202-2. For instance, for a value X (e.g., a value between 0 and 1) for mixing setting 204, combination function 206 may combine first fitting strategy 202-1 and second fitting strategy 202-2 by multiplying X with the values for the parameters for first fitting strategy 202-1 and adding the resulting products to (1-X) multiplied with the values for the parameters for second fitting strategy 202-2. The combined values for each of the parameters may define custom fitting strategy 208, which may be applied to hearing device 102.

By implementing custom fitting strategy 208 in this way, hearing device 102 may allow a user of hearing device 102 to self-fit hearing device 102 to provide sound that is personalized for the user. By using mixing setting 204 to weight first fitting strategy 202-1 and second fitting strategy 202-2 to define custom fitting strategy 208, a number of options provided for the user may be far greater than a limited number of predetermined settings that may be typically provided by conventional hearing devices. Additionally, first fitting strategy 202-1 and second fitting strategy 202-2 may be defined such that a progression from second fitting strategy 202-2 to first fitting strategy 202-1 may model compensation for a progression of hearing loss. Defining fitting strategies 202 in this way may allow for various parameters to be adjusted at differing rates that may more effectively compensate for hearing loss as the hearing loss progresses, rather than tying the various parameters to increasing or decreasing linearly relative to each other or a limited number of predetermined settings defining values for the parameters. Additionally or alternatively, fitting strategies 202 may also account for configurations of hearing device 102, such as a type of hearing device 102, types of receivers selected, venting, etc. Additionally or alternatively, first fitting strategy 202-1 and second fitting strategy 202-2 may be optimized for different preferences of music listening, different types of hearing protection, different virtual sound environments, etc.

Furthermore, allowing the user to self-fit hearing device 102 using mixing setting 204 to define custom fitting strategy 208 may allow for interoperability between the user's self-fitting of hearing device 102 and a hearing health care professional's fitting of hearing device 102. As fitting strategies 202 may include values for the same parameters as those the hearing health care professional may use to fit hearing device 102, any adjustments made by the user via mixing setting 204 may be applied to a fitting performed by the hearing health care professional (e.g., an audiogram based fitting) and vice versa. Additionally or alternatively, hearing device 102 may allow the hearing health care professional to adjust first fitting strategy 202-1 and/or second fitting strategy 202-2. By adjusting first fitting strategy 202-1 and/or second fitting strategy 202-2, the hearing health care professional may adjust the progression of custom fitting strategy 208, which may further personalize hearing device 102 for the user to self-fit, as a path from second fitting strategy 202-2 to first fitting strategy 202-1 may define a hearing loss model that is personalized to the user. Further, adjusting first fitting strategy 202-1 and/or second fitting strategy 202-2 may also allow the hearing health care professional to expand a range of functionality of hearing device 102, for example, by raising a maximum set of values to provide an additional highest amount of amplification that is higher than an initial highest amount of amplification.

Hearing device 102 may receive values for mixing setting 204 in any suitable manner. For example, a computing device running a software application may connect to and communicate with hearing device 102. The user (and/or the hearing health care professional) may provide mixing setting 204 to hearing device via the software application. Such software applications may include mobile device apps, professional fitting software, or any other suitable type of software on any suitable device and/or processor. Additionally or alternatively, hearing device 102 may receive values for mixing setting 204 directly on hearing device 102. For instance, hearing device 102 may provide a mode of operation that allows the user to input and/or adjust mixing setting 204 via buttons, voice commands, or any other suitable interface on hearing device 102. Additionally or alternatively, hearing device 102 may present the user with a plurality of output signals processed with different values for mixing setting 204 and allow the user to set the value for mixing setting 204 by choosing a preference among the plurality of output signals.

Figure 3:
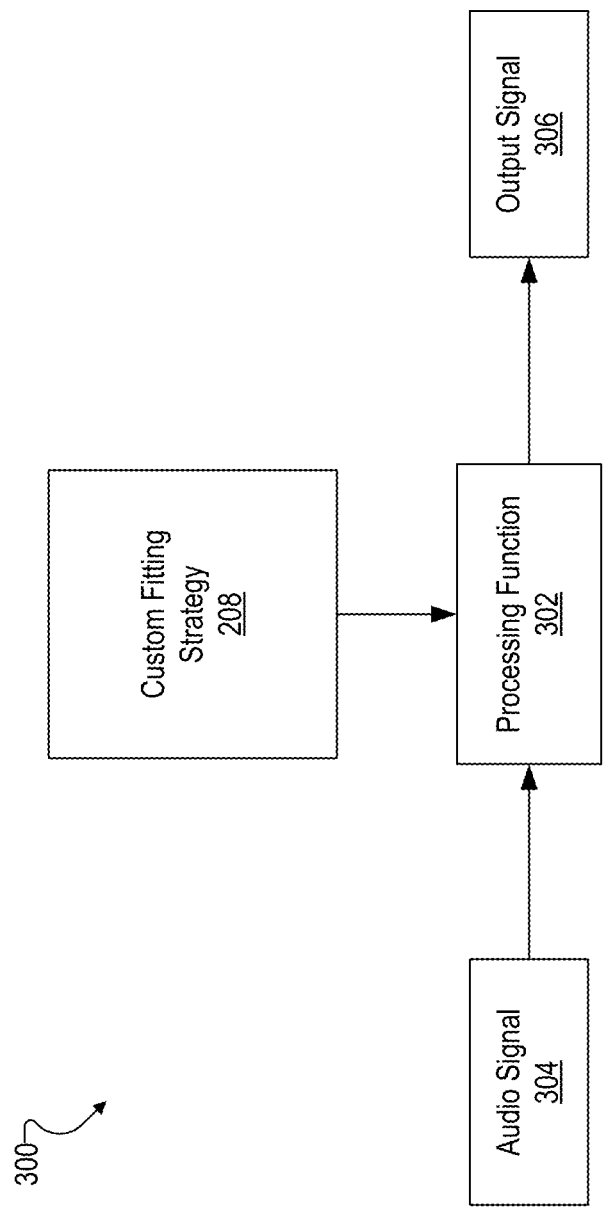

FIG. 3 illustrates an exemplary implementation 300 of a fitting strategy (e.g., custom fitting strategy 208) for a hearing device (e.g., hearing device 102). Implementation 300 includes a processing function 302 configured to receive an audio signal 304 (e.g., from a microphone, from a Bluetooth stream, or from any other suitable audio source) and process audio signal 304 based on custom fitting strategy 208 to generate an output signal 306. For example, processing function 302 may amplify audio signal 304 based on values of parameters provided by custom fitting strategy 208. Custom fitting strategy 208 may specify values for any suitable parameters for processing audio signal 304 as described herein. In some examples, custom fitting strategy 208 may further include a plurality of such sets of values for the plurality of parameters, such as shown in FIG. 4.

Figure 4:
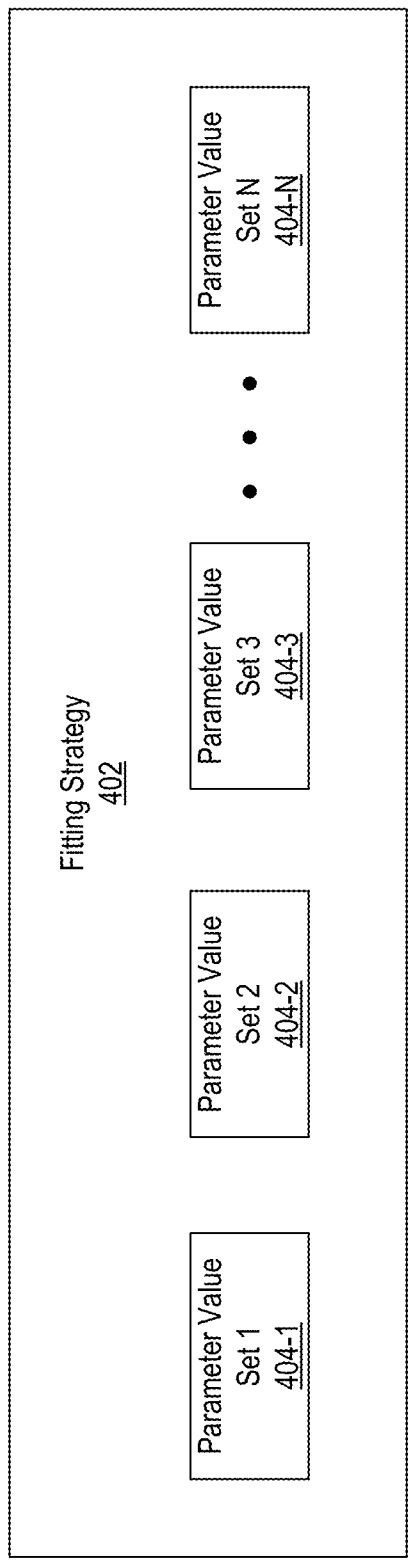

FIG. 4 illustrates an exemplary fitting strategy 402. Fitting strategy 402 may be an implementation of fitting strategies 202 and/or custom fitting strategy 208. Fitting strategy 402 includes parameter value sets 404 (e.g., parameter value set 1 404-1 through parameter value set N 404-N). Each parameter value set of parameter value sets 404 may include values for a plurality of parameters that specify an operation of a hearing device (e.g., hearing device 102) for a respective frequency band. For example, fitting strategy 402 may include N parameter value sets 404, where N equals 20, corresponding to 20 Bark scale bands (or any other suitable frequency band). In this example, parameter value set 1 404-1 may correspond to a first Bark scale band (e.g., a first frequency band centered around a first frequency such as 172 hertz (Hz)). Parameter value set 1 404-1 may include a set of values for a plurality of parameters including, for instance, gain levels, knee points, and compression ratios for processing portions of audio signals in the first Bark scale band for fitting strategy 402.

For example, FIG. 5 shows a chart 500 of an exemplary implementation of fitting strategies for a hearing device (e.g., hearing device 102). Chart 500 shows in a first portion 502-1 example values for a mixing setting (e.g., mixing setting 204), in a second portion 502-2 example values for a first fitting strategy (e.g., first fitting strategy 202-1), and in a third portion 502-3 example values for a second fitting strategy (e.g., second fitting strategy 202-2). Chart 500 shows in columns 504 (e.g., columns 504-1 through 504-20) example parameter value set numbers and corresponding Bark band frequencies. Chart 500 shows in rows 506 (e.g., rows 506-1 through 506-20) example parameters for fitting strategies 202 that specify the operation of hearing device 102. For instance, column 504-1 shows values for a plurality of parameters for a parameter value set (e.g., parameter value set 1 404-1) for a first Bark band centered around a frequency of 172 Hz. Row 506-1 shows a maximum value for a mixing setting (e.g., mixing setting 204) and row 506-2 shows a minimum value for mixing setting 204. In this example, the maximum and minimum values are 1 and 0, respectively, allowing mixing setting 204 to provide a direct weighting value between first fitting strategy 202-1 and second fitting strategy 202-2.

Second portion 502-2 shows example values for first fitting strategy 202-1, which may be a maximum set of values for hearing device 102. For example, row 506-3 shows a value of 95.3 for a parameter labeled SLim (e.g., a maximum power output (MPO)) for the first Bark band. Thus, the maximum MPO for hearing device 102 for the first Bark band would be 95.3, which may refer to a decibel (dB) level. For a second Bark band (e.g., a Bark band centered around a frequency of 345 Hz), the maximum MPO is 94.6 dB, as shown in row 506-3, column 504-2. First fitting strategy 202-1 includes values for gain parameters (e.g., GcLoud, GcMid, GcSoft, GcQuiet) and knee point parameters (e.g., EkLoud, EkMid, EkSoft, EkQuiet). First fitting strategy 202-1 may also include compression ratio parameters that are calculated from the gain and knee point parameters. As shown, first fitting strategy 202-1 includes values for each of these parameters for 20 Bark bands. Each set of values for each of Bark bands 1 through 20 may respectively define a parameter value set for parameter value sets 1 through 20.

Similarly, third portion 502-3 shows example values for second fitting strategy 202-2, which may be a minimum set of values for hearing device 102. Second fitting strategy 202-2 may include values for the same parameters as first fitting strategy 202-1, so that a weighted combination of first fitting strategy 202-1 and second fitting strategy 202-2 may be used to define a custom fitting strategy (e.g., custom fitting strategy 208) also including the same parameters.

Figure 6:
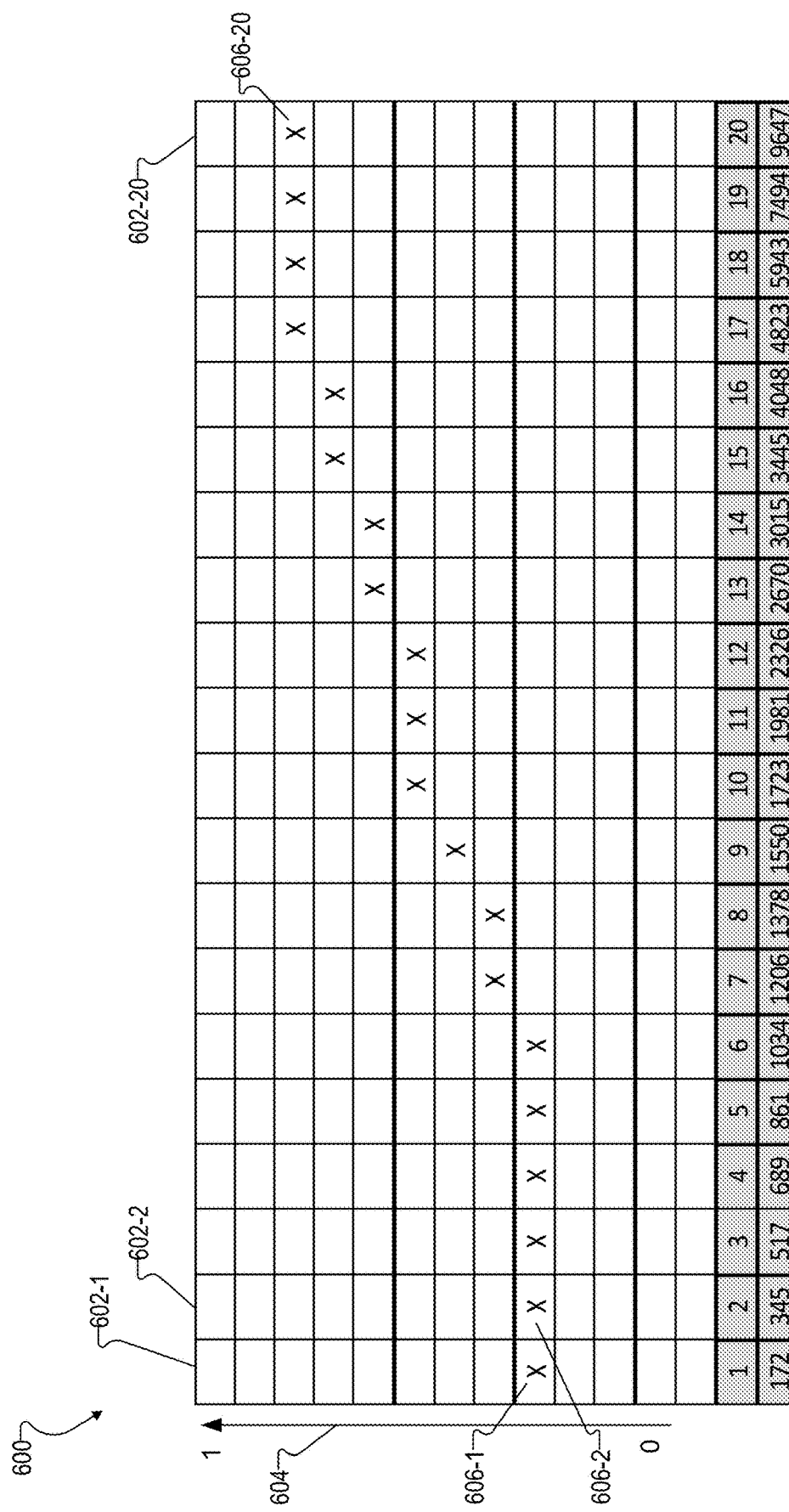

FIG. 6 shows a chart 600 of an example implementation of a mixing setting (e.g., mixing setting 204) for a custom fitting strategy (e.g., custom fitting strategy 208) for a hearing device (e.g., hearing device 102). Chart 600 shows example values for mixing setting 204. Columns 602 (e.g., columns 602-1 through 602-20) show frequency ranges (e.g., Bark bands). A y-axis 604 shows that cells at a bottom of chart 600 correspond to a minimum value for mixing setting 204 (e.g., zero), while cells at a top of chart 600 correspond to a maximum value for mixing setting 204 (e.g., one). Cells 606 (e.g., cells 606-1 through 606-20) within each of columns 602, respectively, are marked with an X to indicate a value for mixing setting 204 for the respective Bark band. The values may specify a weighting of a first fitting strategy (e.g., first fitting strategy 202-1) and a second fitting strategy (e.g., second fitting strategy 202-2) for each of the frequency ranges specified by fitting strategies 202. The values may define an array of values as indicated by cells 606-1 through 606-20 and provided as a single value for mixing setting 204. An example of such an array is shown in FIG. 7.

FIG. 7 shows a chart 700 of another example implementation of a mixing setting (e.g., mixing setting 204) for a custom fitting strategy (e.g., custom fitting strategy 208) for a hearing device (e.g., hearing device 102). Chart 700 shows a single array of values for mixing setting 204. Each of columns 702 (e.g., columns 702-1 through 702-20) corresponds to a frequency range (e.g., a Bark band) as specified by a frequency in Hz in row 704-1 and shows a value in row 704-2 of mixing setting 204 for the corresponding Bark band. For example, column 702-1 shows a value of 0.39 for a first Bark band centered around 172 Hz. Thus, referring back to chart 500 of FIG. 5, a combination function (e.g., combination function 206) of hearing device 102 may receive the value 0.39 of mixing setting 204 and apply 0.39 as a weight with which to multiply values in column 504-1 of portion 502-2 (corresponding to first fitting strategy 202-1). A product of 0.39 and the values of column 504-1 of portion 502-2 may be added to a product of (1-0.39) (i.e., 0.61) and values of column 504-1 of portion 502-3 (corresponding to second fitting strategy 202-2). A sum of the two products may provide values for the first Bark band of custom fitting strategy 208. Such a process may be applied to each of the other Bark bands to generate values for all the parameters for all the frequency ranges of custom fitting strategy 208. The process may be generalized for each of the frequency ranges and for various values of maximum and minimum values for mixing setting 204 using a formula:

$$V_{bb} = X_{bb} \cdot \left( \frac{PN_{maxbb} - PN_{minbb}}{X_{maxbb} - X_{minbb}} \right) + \left( PN_{minbb} - \left( \frac{PN_{maxbb} - PN_{minbb}}{X_{maxbb} - X_{minbb}} \right) \cdot X_{minbb} \right),$$

where $V_{bb}$ is a value for custom fitting strategy 208 for a given parameter for a given Bark band, $X_{bb}$ is a value for mixing setting 204 for the given Bark band, $PN_{maxbb}$ is a maximum value for the given parameter for the given Bark band, $PN_{minbb}$ is a minimum value for the given parameter for the given Bark band, $X_{maxbb}$ is a maximum value for mixing setting 204 for the given Bark band, and $X_{minbb}$ is a minimum value for a mixing setting 204 for the given Bark band.

FIG. 8 shows a chart 800 of another example implementation of fitting strategies for a hearing device (e.g., hearing device 102). Similar to chart 500 of FIG. 5, chart 800 shows in a first portion 802-1 example values for a mixing setting (e.g., mixing setting 204), in a second portion 802-2 example values for a first fitting strategy (e.g., first fitting strategy 202-1), and in a third portion 802-3 example values for a second fitting setting (e.g., second fitting strategy 202-2). Chart 800 shows in columns 804 (e.g., columns 804-1 through 804-20) example parameter value set numbers and corresponding Bark band frequencies. Chart 800 shows in rows 806 (e.g., rows 806-1 through 806-20) example parameters for fitting strategies 202 that specify the operation of hearing device 102. For instance, column 804-1 shows values for a plurality of parameters for a parameter value set (e.g., parameter value set 1 404-1) for a first Bark band centered around a frequency of 172 Hz. Row 806-1 shows a maximum value for a mixing setting (e.g., mixing setting 204) and row 806-2 shows a minimum value for mixing setting 204. The maximum and minimum values may be 1 and 0, respectively as shown, allowing mixing setting 204 may provide a weighting value between first fitting strategy 202-1 and second fitting strategy 202-2.

While chart 500 shows example values for the plurality of parameters for first fitting strategy 202-1 and second fitting strategy 202-2, chart 800 shows example offset values for the plurality of parameters for fitting strategies 202. For instance, while row 506-3 shows values for a maximum power output, row 806-3 shows offset values for a maximum power output (e.g., DMPO). The offset values may specify amounts to be added or subtracted from a predetermined base parameter value set (e.g., a standard base parameter value set, a personalized base parameter value set, a base parameter value set that is determined by a hearing health care professional, etc.). For instance, column 804-1 shows a value of 6 for DMPO for a first Bark band in second portion 802-2 and a value of −12 for DMPO in a third portion 802-3, meaning first fitting strategy 202-1 may include an MPO of a base MPO plus 6 dB while second fitting strategy 202-2 may include an MPO of the base MPO minus 12 dB for the first Bark band. Thus, chart 800 may provide another exemplary way to define fitting strategies 202.

While charts 500, 600, 700, and 800 show example parameters for fitting strategies 202 and 208 with 20 Bark bands, any suitable number of parameter value sets may be used. For example, fitting strategies may use 24 Bark bands or any other number of divisions (including no divisions) of frequency bands. Further, fitting strategies may use a particular number of parameter value sets but receive and/or provide a different number of inputs for the user. For instance, fitting strategy 208 may use 20 Bark bands and receive mixing setting 204 that provides an array of 20 values. However, hearing device 102 and/or a software application communicating with hearing device 102 may present a number other than 20 (e.g., 5 or 10 or any other suitable number) of inputs for the user to provide. Hearing device 102 may group a number of parameter value sets together and apply a same value to the group of parameter value sets. In this example, hearing device 102 (and/or a software application communicating with hearing device 102) may present inputs for 5 values (e.g., 5 input sliders, dials, text boxes, dropdowns, buttons, etc.) and group the 20 Bark bands to the 5 values. Hearing device 102 may group 4 Bark bands per value or any other suitable grouping, such as grouping Bark bands that correlate more closely with one another. Additionally or alternatively, hearing device 102 (and/or a software application communicating with hearing device 102) may present an input for a loudness value, which may provide an overall offset across all frequency bands, and an input for a tilt value, which may provide values for the parameters in each of the frequency bands relative to one another.

Figure 9:
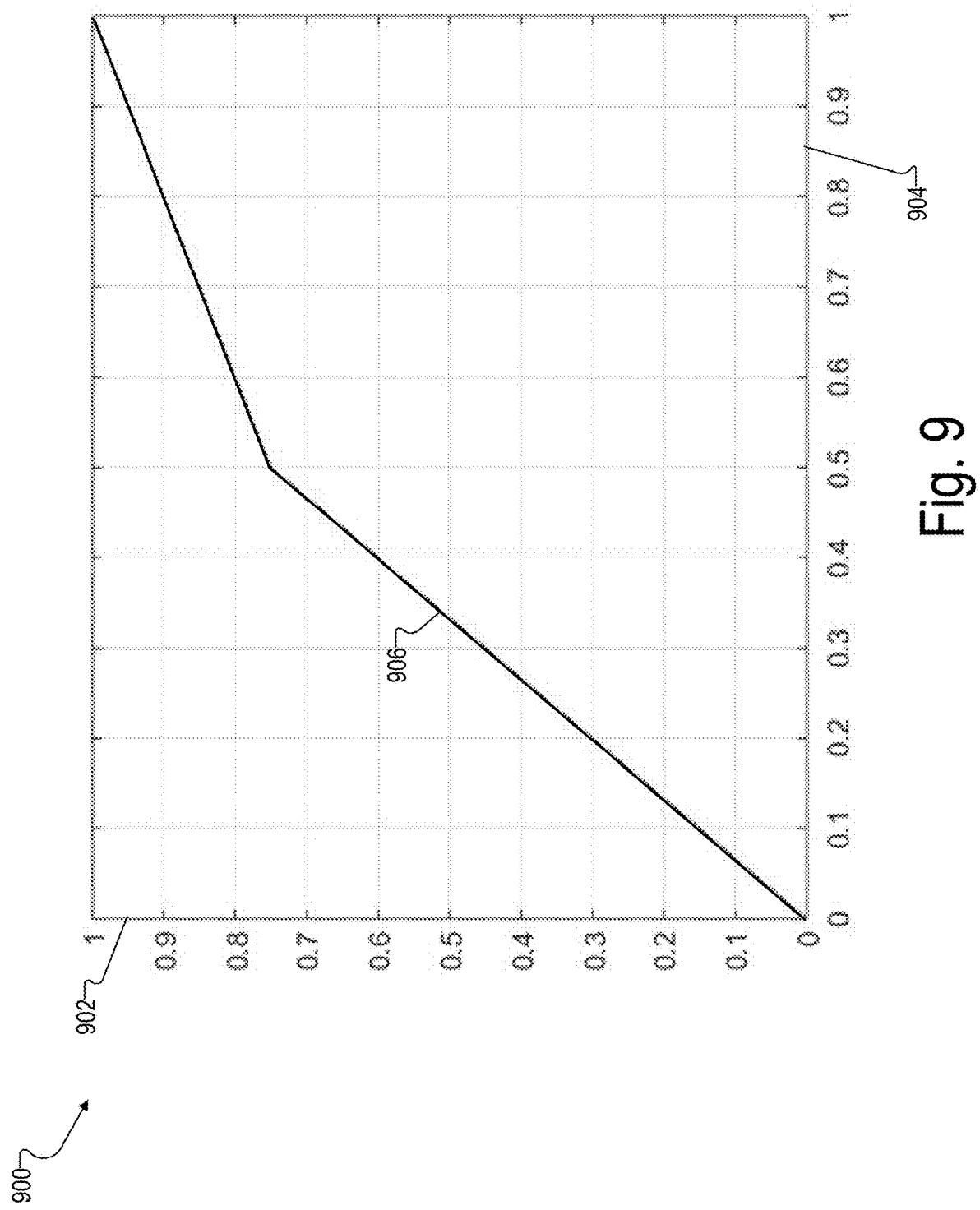
FIGS. 9-10 illustrate exemplary implementations of a mixing setting for a fitting strategy for a hearing device according to principles described herein.

FIG. 9 shows a graph 900 of another exemplary mixing setting (e.g., mixing setting 204) for a custom fitting strategy (e.g., custom fitting strategy 208) for a hearing device (e.g., hearing device 102). Graph 900 shows an example scale of mixing setting 204, showing that mixing setting may increase non-linearly. Graph 900 shows a line 906 that maps the scale of mixing setting 204, plotting output weighting values on a y-axis 902 against input values on an x-axis 904. With a linear scale of mixing setting 204, a value of mixing setting 204 may directly and/or linearly represent a weighting value that is used to weight a first fitting strategy and a second fitting strategy to determine custom fitting strategy 208. However, graph 900 shows that the scale may be non-linear, for instance, if a non-linear scale may more accurately model hearing loss than a linear scale. Line 906 shows a point where x=0.5 that a slope of line 906 changes. The scale of mixing setting 204 in line 906 may be defined with a midpoint between a minimum value and a maximum value for mixing setting 204, where the weighting value used to weight fitting strategies 202 may scale differently depending on whether a value of mixing setting 204 is greater or less than the midpoint. Such a scale may be defined as $$y[k]=m_h[k] \cdot x[k]+b_h[k] \text{ when } x[k] \geq X_{mid}[k],$$

$$y[k]=m_l[k] \cdot x[k]+b_l[k] \text{ otherwise,}$$

where $X_{mid}[k]$ is the midpoint and where $$m_h[k] = \frac{Y_{max}[k] - Y_{mid}[k]}{X_{max}[k] - X_{mid}[k]}, \quad b_h[k] = Y_{max}[k] - m_h[k] \cdot X_{max}[k],$$

$$m_l[k] = \frac{Y_{mid}[k] - Y_{min}[k]}{X_{mid}[k] - X_{min}[k]}, \quad b_l[k] = Y_{mid}[k] - m_l[k] \cdot X_{mid}[k].$$

While graph 900 shows line 906 with one midpoint, any suitable number of midpoints may be used to define the scale of mixing setting 204.

Figure 10:
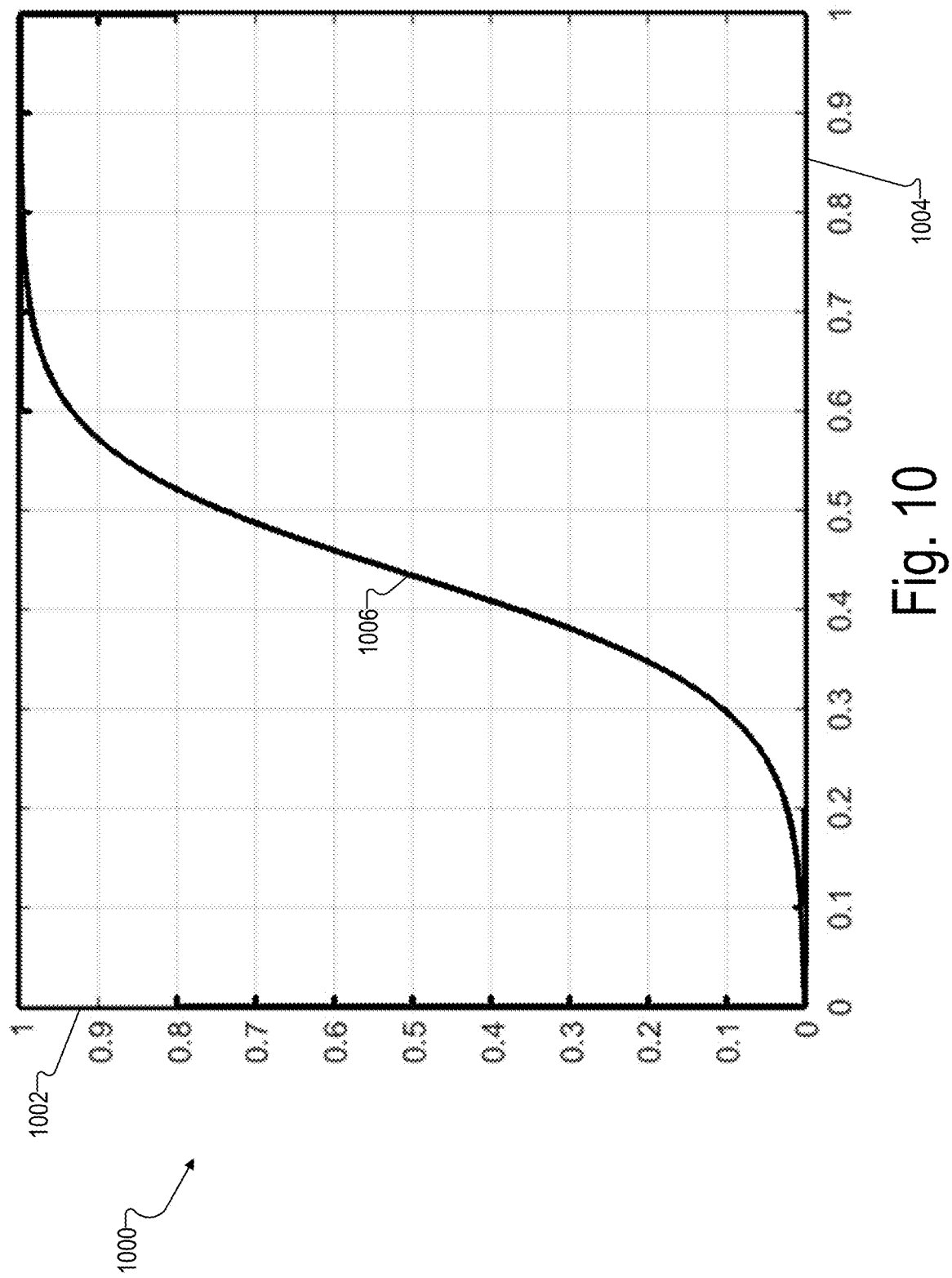

FIG. 10 shows a graph 1000 of another exemplary mixing setting (e.g., mixing setting 204) for a custom fitting strategy (e.g., custom fitting strategy 208) for a hearing device (e.g., hearing device 102). Graph 1000 shows another example non-linear scale for mixing setting 204. Graph 1000 shows a curve 1006 that maps the scale of mixing setting 204, plotting output weighting values on a y-axis 1002 against input values on an x-axis 1004. Curve 1006 may represent a generalized logistic function. The generalized logistic function may be defined as $$A + \frac{K - A}{(C + Qe^{-B(x-M)})^{1/v}}$$

Where A, B, C, K, Q, M, and v are parameters for defining a shape of the generalized logistic function. For instance, for curve 1006, A=0, K=1, C=1, Q=0.35, B=16, M=0.5, and v=1. Such a non-linear scale may in some instances better model hearing loss and/or hearing loss compensation than a linear scale.

Figure 11:
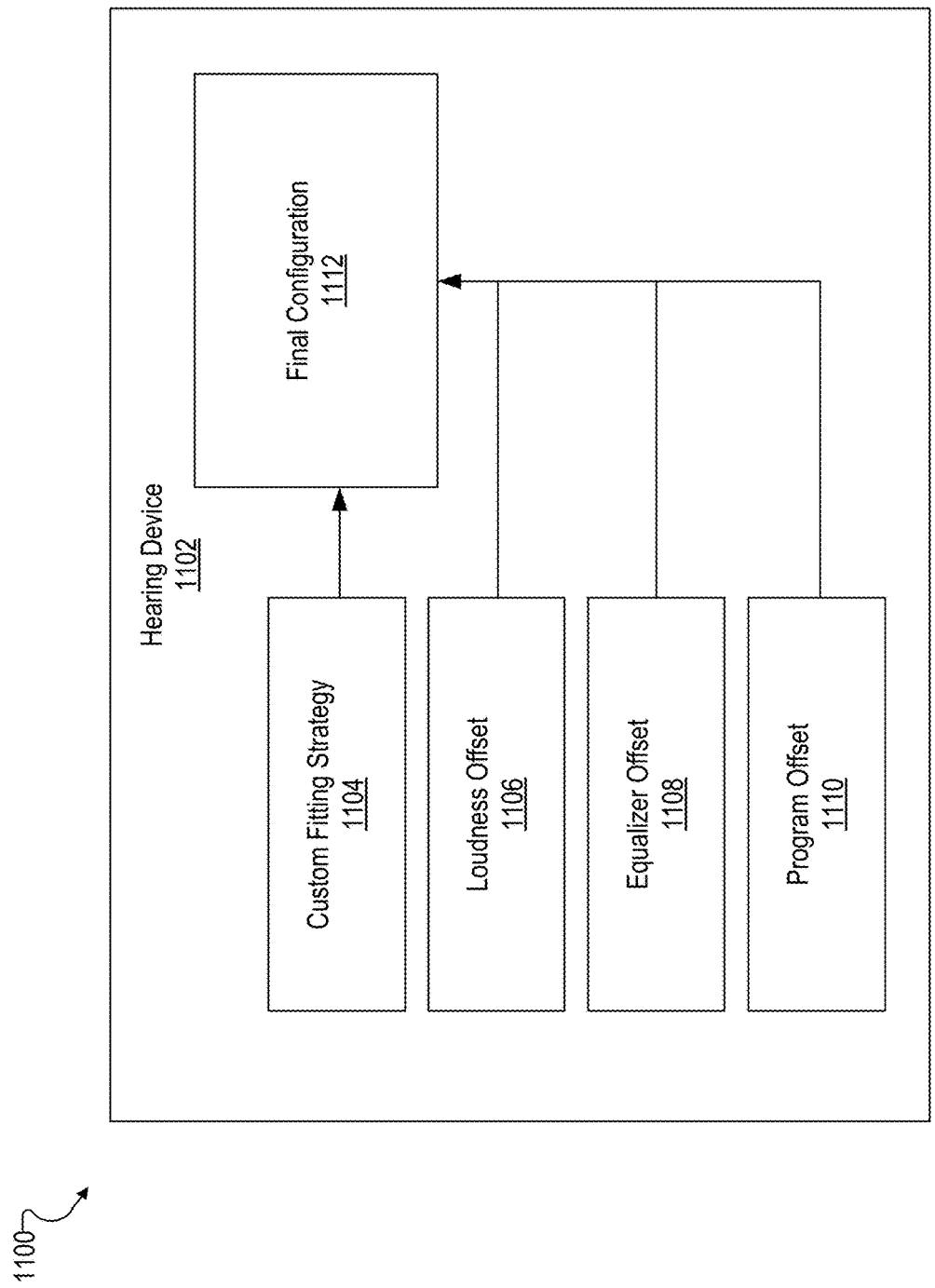
FIGS. 11-12 illustrate exemplary implementations of a hearing device according to principles described herein.

FIG. 11 shows an exemplary implementation 1100 of a hearing device 1102 (e.g., an implementation of hearing device 102). Hearing device 1102 includes a custom fitting strategy 1104 (e.g., an implementation of custom fitting strategy 208). As shown, in some examples, hearing device 1102 provides output signals based on custom fitting strategy 1104 as well as additional parameters. Hearing device 1102 may combine and/or adjust custom fitting strategy 1104 based on any suitable additional parameters, such as runtime parameters including a loudness offset 1106, an equalizer offset 1108, and/or a program offset 1110 to generate a final configuration 1112 used to process input audio signals to provide the output signals. Runtime parameters may include any suitable parameters that may be determined during runtime of hearing device 102, which may be influenced by factors such as an environment of a user, an activity of the user, a preference of the user, etc.

For example, loudness offset 1106 may adjust custom fitting strategy 1104 by providing an additional offset that raises or lowers all values of the parameters of custom fitting strategy 1104. Alternatively, if custom fitting strategy 1104 is defined using a loudness value (corresponding to an overall offset) and a tilt value (corresponding to parameter values of Bark bands relative to one another), loudness offset 1106 may adjust the loudness value. Loudness offset 1106 may be applied by the user and/or automatically applied by hearing device 102 based on the environment and/or activity of the user (e.g., if the user is in a loud environment, if the user is listening to a device while running, etc.).

Equalizer offset 1108 may adjust custom fitting strategy 1104 based on frequency bands. For instance, an example of equalizer offset 1106 may raise bass levels while lowering treble levels and keeping mid levels the same. Any such suitable equalizer offsets 1108 may be applied by the user and/or automatically applied by hearing device 102 (e.g., based on a detection of a type of input (e.g., music, speech) to be processed by hearing device 102).

Program offset 1110 may adjust custom fitting strategy 1110 based on the environment and/or activity of the user. For example, program offsets 1110 may include sound processing profiles optimized for speech, quiet environments, loud environments, vehicular environments, etc. Any such suitable program offsets 1110 may be applied by the user and/or automatically applied by hearing device 102 based on detection of appropriate environments and/or activities.

Figure 12:
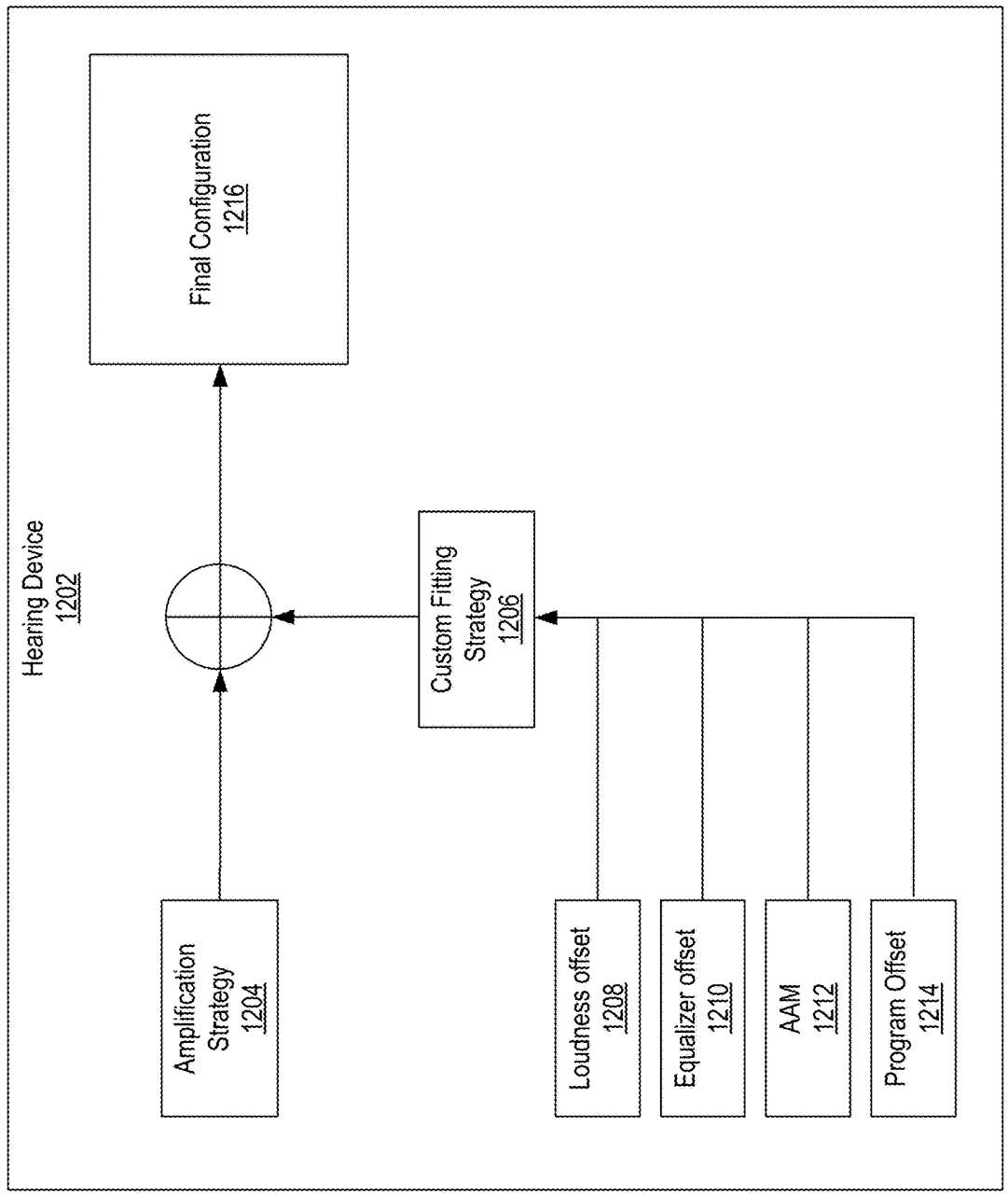

FIG. 12 shows another exemplary implementation 1200 of a hearing device 1202 (e.g., an implementation of hearing device 102). Hearing device 1202 includes an amplification strategy 1204, which may include a set of values for parameters that specify an operation of hearing device 1202. For example, amplification strategy 1204 may be a standard set of values for the parameters. Hearing device 1202 further includes a custom fitting strategy 1206 (e.g., an implementation of custom fitting strategy 208), which may be combined with amplification strategy 1204 to determine a final configuration 1216 that is used to process audio signals.

As described herein, custom fitting strategy 1206 may include one or more sets of values for the parameters that specify the operation of hearing device 1202. Custom fitting strategy 1206 may be determined by a mixing setting (e.g., mixing setting 204) that specifies a weight between a first fitting strategy (e.g., first fitting strategy 202-1) and a second fitting strategy (e.g., second fitting strategy 202-2). A value for mixing setting may include a single value (e.g., one number or an array of values) or values for several parameters that define the value for mixing setting 204. For example, mixing setting 204 may be determined by a loudness offset 1208 and an equalizer offset 1210 (e.g., a tilt value specifying values for parameters based on frequency ranges relative to one another).

In some examples, custom fitting strategy 1206 may also include other parameters and/or offsets that adjust or are combined with a weighted combination of first and second fitting strategies. As shown, custom fitting strategy 1206 further includes an automatic adaptation manager (AAM) 1212 and a program offset 1214. AAM 1212 may adjust an overall gain of custom fitting strategy 1206 to gradually increase over time to allow a user to grow accustomed to amplification provided by hearing device 1202. AAM 1212 may be implemented in any suitable way. Program offset 1214 may adjust custom fitting strategy 1206 based on the environment and/or activity of the user, as described herein.

Figure 13:
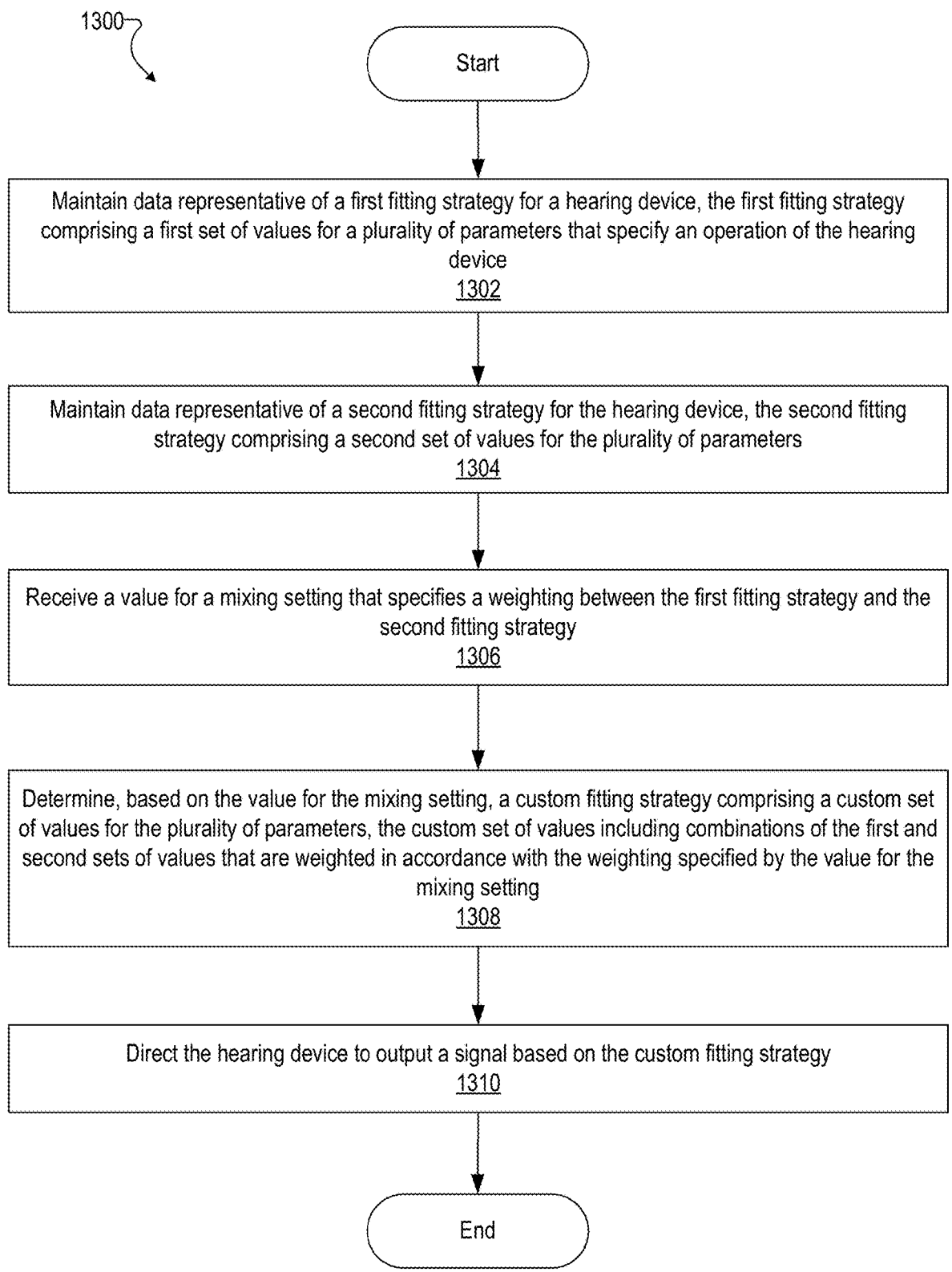
FIG. 13 illustrates an exemplary method according to principles described herein.

FIG. 13 illustrates an exemplary method 1300. One or more of the operations shown in FIG. 13 may be performed by any of the hearing devices described herein. While FIG. 13 illustrates exemplary operations according to one embodiment, other embodiments may omit, add to, reorder, and/or modify any of the operations shown in FIG. 13.

In step 1302, a processor of a hearing device maintains data representative of a first fitting strategy for the hearing device, the first fitting strategy comprising a first set of values for a plurality of parameters that specify an operation of the hearing device. Step 1302 may be performed in any of the ways described herein.

In step 1304, the processor maintains data representative of a second fitting strategy for the hearing device, the second fitting strategy comprising a second set of values for the plurality of parameters. Step 1304 may be performed in any of the ways described herein.

In step 1306, the processor receives a value for a mixing setting that specifies a weighting between the first fitting strategy and the second fitting strategy. Step 1306 may be performed in any of the ways described herein.

In step 1308, the processor determines, based on the value for the mixing setting, a custom fitting strategy comprising a custom set of values for the plurality of parameters, the custom set of values including combinations of the first and second sets of values that are weighted in accordance with the weighting specified by the value for the mixing setting. Step 1308 may be performed in any of the ways described herein.

In step 1310, the processor directs the hearing device to output a signal based on the custom fitting strategy. Step 1310 may be performed in any of the ways described herein.

Figure 14:
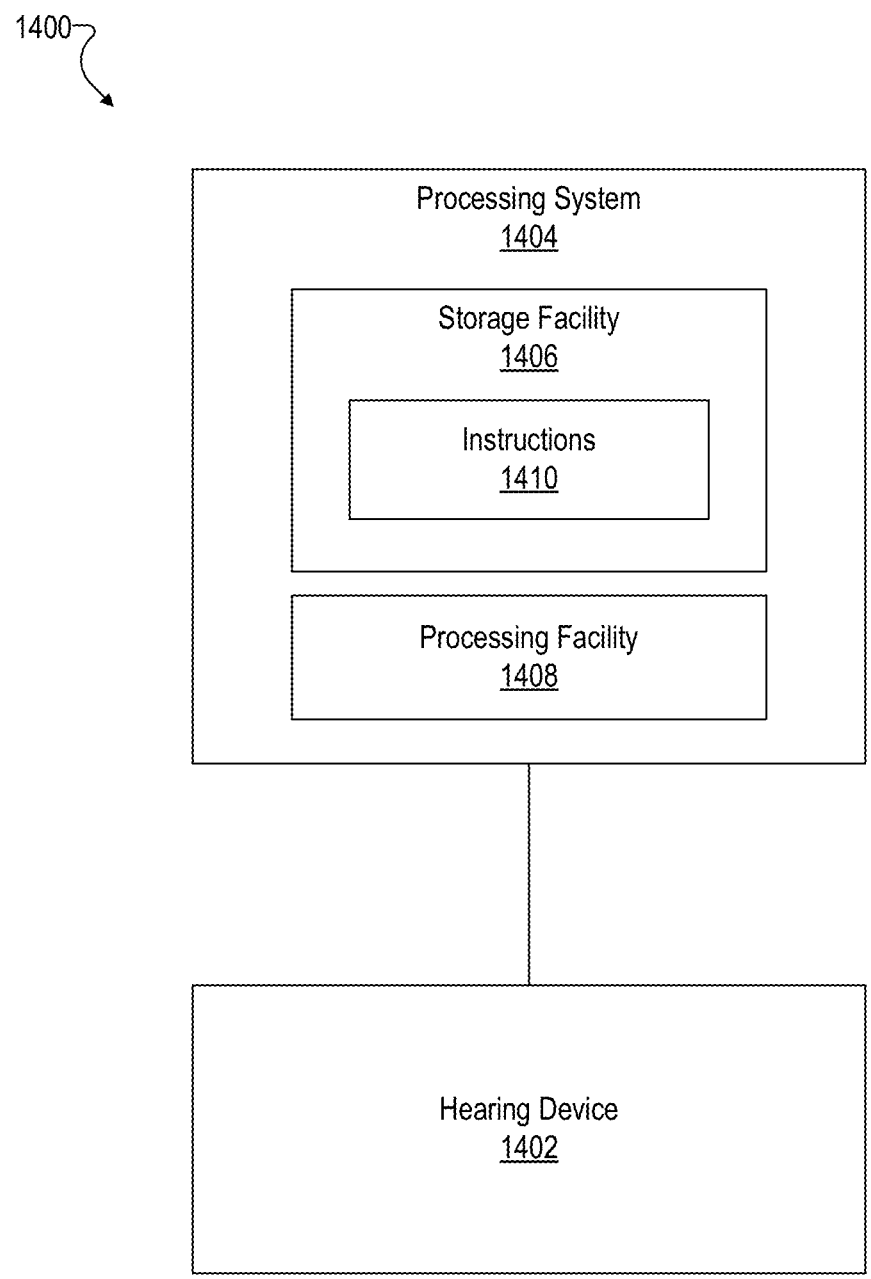
FIG. 14 illustrates an exemplary configuration of a hearing device according to principles described herein.

FIG. 14 shows an exemplary configuration 1400 of a hearing device 1402 (e.g., an implementation of hearing device 102). Hearing device 1402 is communicatively coupled to a processing system 1404, which may be configured to allow a user to personalize a fit of hearing device 1402. Processing system 1404 may be communicatively coupled to hearing device 1402 in any suitable manner, such as a wireless or wired connection.

Processing system 1404 may be implemented by any suitable computing device, such as a mobile device, a laptop, a tablet, a smart watch, a fitting device used by a hearing health care professional, etc. Processing system 1404 includes a storage facility 1406 and a processing facility 1408 selectively and communicatively coupled to one another. Each of facilities 1406 and 1408 may include or be implemented by one or more physical computing devices including hardware and/or software components such as processors, memories, storage drives, communication interfaces, instructions stored in memory for execution by the processors, and so forth. Although facilities 1406 and 1408 are shown to be separate facilities in FIG. 14, facilities 1406 and 1408 may be combined into fewer facilities, such as into a single facility, or divided into more facilities as may serve a particular implementation. In some examples, each of facilities 1406 and 1408 may be distributed between multiple devices and/or multiple locations as may serve a particular implementation.

Storage facility 1406 may maintain (e.g., store) executable data used by processing facility 1408 to perform any of the operations described herein. For example, storage facility 1406 may store instructions 1410 that may be executed by processing facility 1408 to perform any of the operations described herein. Instructions 1410 may be implemented by any suitable application, software, code, and/or other executable data instance.

Storage facility 1406 may also maintain any data received, generated, managed, used, and/or transmitted by processing facility 1408. For example, storage facility 1406 may maintain fitting strategy data, mixing setting data, hearing device parameter data, sound processing algorithms, hearing loss compensation data, audio processing data, and the like.

Processing facility 1408 may be configured to perform (e.g., execute instructions 1410 stored in storage facility 1406 to perform) various processing operations associated with fitting hearing device 1402 as described herein. For example, processing facility 1408 may be configured to receive a value for a mixing setting that specifies a weighting between a first fitting strategy for a hearing device communicatively coupled to the computing device and a second fitting strategy for the hearing device, the first fitting strategy comprising a first set of values for a plurality of parameters that specify an operation of the hearing device and the second fitting strategy comprising a second set of values for the plurality of parameters. Processing facility 1408 may be further configured to determine, based on the value for the mixing setting, a custom fitting strategy comprising a custom set of values for the plurality of parameters, the custom set of values including combinations of the first and second sets of values that are weighted in accordance with the weighting specified by the value for the mixing setting. Processing facility 1408 may be further configured to transmit a command to the hearing device to operate based on the custom fitting strategy.

Figure 15:
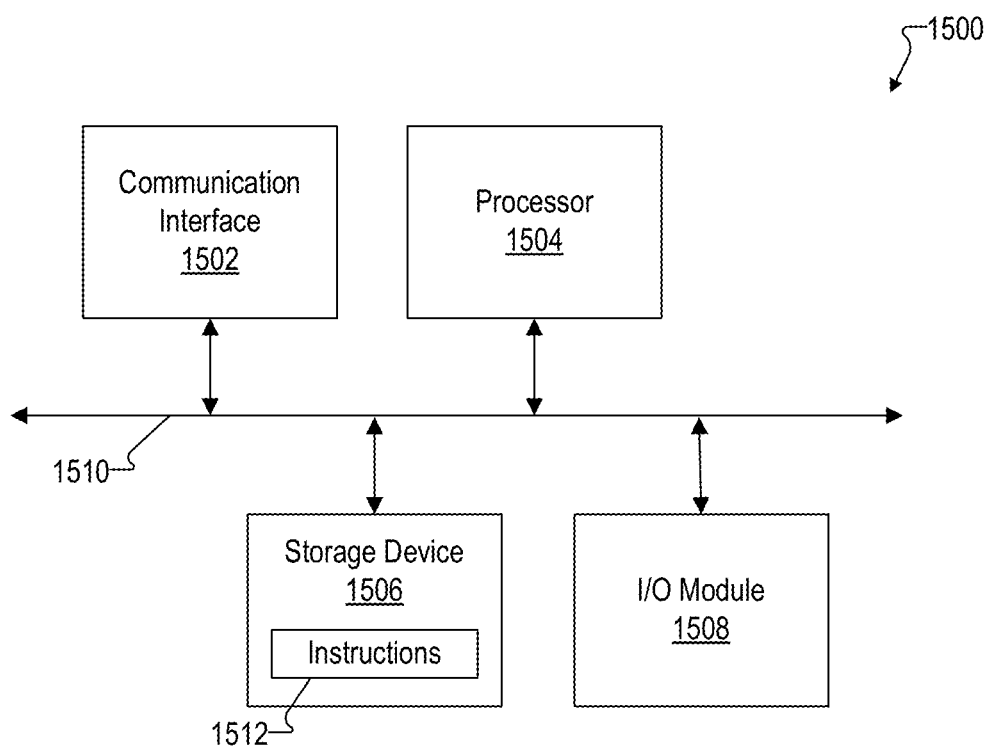
FIG. 15 illustrates an exemplary computing system according to principles described herein.

FIG. 15 illustrates an exemplary computing device 1500 that may be specifically configured to perform one or more of the processes described herein. As shown in FIG. 15, computing device 1500 may include a communication interface 1502, a processor 1504, a storage device 1506, and an input/output ("I/O") module 1508 communicatively connected one to another via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data and/or interpreting, executing, and/or directing execution of one or more of the instructions, processes, and/or operations described herein. Processor 1504 may perform operations by executing computer-executable instructions 1512 (e.g., an application, software, code, and/or other executable data instance) stored in storage device 1506.

Storage device 1506 may include one or more data storage media, devices, or configurations and may employ any type, form, and combination of data storage media and/or device. For example, storage device 1506 may include, but is not limited to, any combination of the non-volatile media and/or volatile media described herein. Electronic data, including data described herein, may be temporarily and/or permanently stored in storage device 1506. For example, data representative of computer-executable instructions 1512 configured to direct processor 1504 to perform any of the operations described herein may be stored within storage device 1506. In some examples, data may be arranged in one or more databases residing within storage device 1506.

I/O module 1508 may include one or more I/O modules configured to receive user input and provide user output. I/O module 1508 may include any hardware, firmware, software, or combination thereof supportive of input and output capabilities. For example, I/O module 1508 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In some examples, any of the systems, computing devices, processors, controller units, and/or other components described herein may be implemented by computing device 1500. For example, processing system 1404 may be implemented by processor 1504.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A hearing device comprising:
a memory storing instructions; and
a processor communicatively coupled to the memory and configured to execute the instructions to:
maintain data representative of a first fitting strategy for the hearing device, the first fitting strategy comprising a first set of values for a plurality of parameters that specify an operation of the hearing device;
maintain data representative of a second fitting strategy for the hearing device, the second fitting strategy comprising a second set of values for the plurality of parameters;

receive a value for a mixing setting that specifies a weighting between the first fitting strategy and the second fitting strategy;

determine, based on the value for the mixing setting, a custom fitting strategy comprising a custom set of values for the plurality of parameters, the custom set of values including combinations of the first and second sets of values that are weighted in accordance with the weighting specified by the value for the mixing setting; and direct the hearing device to output a signal based on the custom fitting strategy.

2. The hearing device of claim 1, wherein:

the first set of values includes minimum values for the hearing device for each of the plurality of parameters; and the second set of values includes maximum values for the hearing device for each of the plurality of parameters.

3. The hearing device of claim 1, wherein:

the first set of values optimizes the hearing device for a first environment; and the second set of values optimizes the hearing device for a second environment.

4. The hearing device of claim 1, wherein:

the first set of values includes a first subset of values for the plurality of parameters that correspond to a first frequency range and a second subset of values for the plurality of parameters that correspond to a second frequency range;

the second set of values includes a third subset of values for the plurality of parameters that correspond to the first frequency range and a fourth subset of values for the plurality of parameters that correspond to the second frequency range;

the mixing setting includes an array of values;

the receiving the value for the mixing setting includes receiving a first value of the array of values, the first value corresponding to the first frequency range, and a second value of the array of values, the second value corresponding to the second frequency range; and the determining the custom fitting strategy includes weighting the first subset and the third subset in accordance with the first value for the mixing setting and weighting the second subset and the fourth subset in accordance with the second value for the mixing setting.

5. The hearing device of claim 4, wherein the first value or the second value of the array of values for the mixing setting additionally corresponds to a third frequency range.

6. The hearing device of claim 4, wherein the receiving the first and second values of the array of values for the mixing setting includes:

receiving a loudness value that specifies an offset for the first value and the second value; and receiving a tilt value that specifies values for the first value and the second value relative to each other.

7. The hearing device of claim 1, wherein the receiving the value for the mixing setting includes:

receiving an audiogram; and determining the value based on the audiogram.

8. The hearing device of claim 1, wherein a scale of the mixing setting corresponds to a non-linear combination of the first fitting strategy and the second fitting strategy.

9. The hearing device of claim 1, wherein at least one of the first fitting strategy, the second fitting strategy, and a scale of the mixing setting is determined based on a hearing loss compensation model.

10. The hearing device of claim 1, wherein the processor is further configured to execute the instructions to:

adjust the combinations of the plurality of parameters based on runtime parameters.

11. The hearing device of claim 10, wherein the runtime parameters include at least one of a loudness offset, an equalizer offset, and a sound processing program offset.

12. The hearing device of claim 1, wherein the receiving the value for the mixing setting includes receiving data from a computing device communicatively coupled to the hearing device.

13. The hearing device of claim 1, wherein the receiving the value for the mixing setting includes receiving inputs via an interface on the hearing device.

14. A method comprising:

maintaining, by a hearing device, data representative of a first fitting strategy for the hearing device, the first fitting strategy comprising a first set of values for a plurality of parameters that specify an operation of the hearing device;

maintaining, by the hearing device, data representative of a second fitting strategy for the hearing device, the second fitting strategy comprising a second set of values for the plurality of parameters;

receiving, by the hearing device, a value for a mixing setting that specifies a weighting between the first fitting strategy and the second fitting strategy;

determining, by the hearing device and based on the value for the mixing setting, a custom fitting strategy comprising a custom set of values for the plurality of parameters, the custom set of values including combinations of the first and second sets of values that are weighted in accordance with the weighting specified by the value for the mixing setting; and outputting, by the hearing device, a signal based on the custom fitting strategy.

15. The method of claim 14, wherein:

the first set of values includes minimum values for the hearing device for each of the plurality of parameters; and the second set of values includes maximum values for the hearing device for each of the plurality of parameters.

16. The method of claim 14, wherein:

the first set of values includes a first subset of values for the plurality of parameters that correspond to a first frequency range and a second subset of values for the plurality of parameters that correspond to a second frequency range;

the second set of values includes a third subset of values for the plurality of parameters that correspond to the first frequency range and a fourth subset of values for the plurality of parameters that correspond to the second frequency range;

the mixing setting includes an array of values;

the receiving the value for the mixing setting includes receiving a first value of the array of values, the first value corresponding to the first frequency range, and a second value of the array of values, the second value corresponding to the second frequency range; and the determining the custom fitting strategy includes weighting the first subset and the third subset in accordance with the first value for the mixing setting and weighting the second subset and the fourth subset in accordance with the second value for the mixing setting.

17. The method of claim 16, wherein the receiving the first and second values of the array of values for the mixing setting includes:
    receiving a loudness value that specifies an offset for the first value and the second value; and
    receiving a tilt value that specifies values for the first value and the second value relative to each other.

18. The method of claim 14, wherein the receiving the value for the mixing setting includes:
    receiving an audiogram; and
    determining the value based on the audiogram.

19. The method of claim 14, further comprising:
    receiving, by the hearing device, an adjustment to at least one of the first fitting strategy, the second fitting strategy, and the mixing setting.

20. A computing device comprising:
    a memory storing instructions; and
    a processor communicatively coupled to the memory and configured to execute the instructions to:
        receive a value for a mixing setting that specifies a weighting between a first fitting strategy for a hearing device communicatively coupled to the computing device and a second fitting strategy for the hearing device, the first fitting strategy comprising a first set of values for a plurality of parameters that specify an operation of the hearing device and the second fitting strategy comprising a second set of values for the plurality of parameters;
        determine, based on the value for the mixing setting, a custom fitting strategy comprising a custom set of values for the plurality of parameters, the custom set of values including combinations of the first and second sets of values that are weighted in accordance with the weighting specified by the value for the mixing setting; and
        transmit a command to the hearing device to operate based on the custom fitting strategy.

* * * * *